(12) United States Patent
Kubota et al.

(10) Patent No.: US 6,448,289 B1
(45) Date of Patent: Sep. 10, 2002

(54) METHOD FOR REPELLING ARTHROPODS

(75) Inventors: Shunichi Kubota, Minoo; Yoshinori Shono, Sanda, both of (JP)

(73) Assignee: Sumitomo Chemical Co,. Ltd., Osaka (JP)

( * ) Notice: Subject to any disclaimer, the term of this patent is extended or adjusted under 35 U.S.C. 154(b) by 0 days.

(21) Appl. No.: 09/920,815

(22) Filed: Aug. 3, 2001

(30) Foreign Application Priority Data

Aug. 31, 2000 (JP) ........................................ 2000-262678

(51) Int. Cl.7 ................................................ A01N 43/16
(52) U.S. Cl. ....................................................... 514/460
(58) Field of Search ......................................... 514/460

(56) References Cited

FOREIGN PATENT DOCUMENTS

| EP | 0 841 063 A1 | 5/1998 |
|---|---|---|
| JP | 50-24436 A | 3/1975 |
| JP | 51-19126 | 2/1976 |
| JP | 7-126110 | 5/1995 |
| JP | 10-130114 | 5/1998 |
| WO | 88/10258 | 12/1988 |

OTHER PUBLICATIONS

D. Rijke et al., Acidic Components in Essential Oils of Costus Root, Patchouli and Olibanum, Phytochemistry, vol. 17, (1978), pp. 1664–1666.

S. Nakahara et al., "Acidic Compounds in Patchouli Oil", Phytochemistry, vol. 14, (1978), 2712–2713.

*Primary Examiner*—Allen J. Robinson
(74) *Attorney, Agent, or Firm*—Sughrue Mion, PLLC

(57) ABSTRACT

It is possible to repel arthropod by applying 4-hydroxy-6-methyl-3-(4- methylpentanoyl)-2-pyrone of formula:

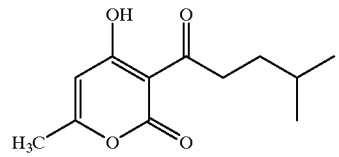

to a place where it is desired to repel arthropods.

5 Claims, No Drawings

METHOD FOR REPELLING ARTHROPODS

FIELD OF THE INVENTION

The present invention relates to a method for repelling arthropods which comprise using 4-hydroxy-6-methyl-3-(4-methylpentanoyl)-2-pyrone as an active ingredient.

Background Arts

Hitherto, repellents those are directly applied to skin or clothes have been utilized for protecting humans or animals from blood-sucking of mosquitoes, flies, acarina and so on. Further, repellents those are applied to specific areas are also utilized for preventing unpleasant arthropods such as centipedes and pill bugs and insanitary insects such as cockroaches from getting indoors.

N,N-diethyl-m-toluamide (hereinafter, referred to as DEET) is mainly used as a repellent for blood-sucking arthropods such as mosquitoes, stable flies and a kind of blood-sucking mite (*Ornithonyssus bacoti*) and insanitary or unpleasant flying insects such as houseflies. As a cockroach repellent, 2-(octylthio)ethanol (MGK-R874: hereinafter, referred to as MGK874) and so on are used. However, these repellents may be effective for only small kinds of arthropods, or the effectiveness is insufficient at rapid effect or long-term effect.

On the other hand, 4-hydroxy-6-methyl-3-(4-methylpentanoyl)-2-pyrone of formula:

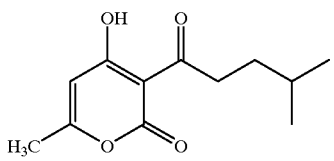

is known as an acidic compound in patchouli oil [Phytochemistry, vol. 14, pp. 2712–2713 (1975)].

SUMMARY OF THE INVENTION

The present invention provides a new use of 4-hydroxy-6-methyl-3-(4-methylpentanoyl)-2-pyrone (hereinafter, referred to as Compound [A]), that is, the present invention is a method for repelling arthropods which comprises applying an effective amount of Compound [A] to a place where it is desired to repel arthropods.

DETAILED DESCRIPTION OF THE INVENTION

Examples of arthropods which the present method repels effectively include dipteran insects such as Culicidae (mosquitoes) [*Anopheles* spp., *Aedes* spp. (e.g. *Aedes aegypti*, *Aedes albopictus*), *Culex* spp. (e.g. *Culex pipiens pallens*, *Culex tritaeniorhynchus*) and so on], Simuliidae (black flies), Stomoxyidae (stable flies), Psychodidae (sand flies), Ceratopogonidae (biting midges), Muscidae and Drosophilidae; dictyopteran insects such as *Blattella germanica* (German cockroach), *Periplaneta fuliginosa* (smokybrown cockroach), *Periplaneta americana* (American cockroach), *Periplaneta brunnea* (brown cockroach) and *Blatta orientalis* (oriental cockroach); coleopteran insects such as *Sitophilus zeamais* (maize weevil), *Callosobruchus chinensis* (adzuki bean weevil), *Tribolium castaneum* (red flour beetle), *Attagenus unicolor japonicus* (black carpet beetle), *Authrenus verbasci* (varied carpet beetle), Anobiidae, Lyctidae (powderpost beetles) and *Paederus fuscipes* (robe beetle); hymenopteran insects such as Formicidae (ants) and Bethylidae; siphonapteran insects such as *Ctenocephalides felis* (cat flea) and *Pulex irritans* (human flea); anopluran insects such as *Pediculus humanus* (body louse) and *Pthirus pubis* (crab louse); isopteran insects such as *Reticulitermes speratus* and *Coptotermes formosanus*; mites such as Acaridae, Pyroglyphidae, Cheyletidae, *Ornithonyssus bacoti* and Trombiculidae; ticks such as *Boophilus microplus* and *Haemaphysalis longiconis*; wood lice; pill bugs; Chilopoda (centipedes); Diplopoda (millipedes) and spiders.

It is possible to use Compound [A] itself for the present repelling method, but Compound [A] is usually to be used as its formulations.

The formulations may be liquid formulation (e.g. emulsifiable concentrates, oil solutions), cream formulation or solid formulation (e.g. wettable powders, water-soluble powders), and usually contains 0.01 to 95% by weight of Compound [A] as an active ingredient. The formulations can be prepared by conventional methods, for example, by mixing Compound [A] with carrier, and optionally surfactant and auxiliaries. Such auxiliaries are sticking agents, dispersants, spreading agents, wetting agents, stabilizers, preservatives and so on.

Examples of carriers include water, alcohols (e.g. methanol, ethanol, isopropyl alcohol, higher alcohols, polyethylene glycol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate), nitriles (e.g. acetonitrile, isobutyronitrile), ethers (e.g. diisopropyl ether, dioxane), amides (e.g. N,N-dimethylformamide, N,N-dimethylacetamide), halogenated hydrocarbons (e.g. dichloromethane, trichloroethane, carbon tetrachloride), dimethyl sulfoxide, vegetable oils (e.g. soybean oil, cottonseed oil, etc.).

Examples of surfactants include sodium salts of higher fatty acids; polyoxyethylene alkyl ethers such as polyoxyetylene oleyl ether; polyoxyethylene alkyl aryl ethers such as polyoxyetylene nonyl phenyl ether; polyoxyetylene fatty acid esters; fatty acid glycerides; sorbitan fatty acid esters; sulfate esters of higher alcohol; and alkylarylsulfonate salts such as sodium dodecylbenzenesulfonate. Examples of sticking agents and dispersants include casein, gelatin, polysaccharides (e.g. starch powder, gum arabic, carboxymethylcellulose, hydroxypropylcellulose, alginic acid), lignin derivatives, sugars and synthetic water-soluble polymers (e.g. polyvinyl alcohol, polyvinylpyrrolidone, polyacrylic acids, carboxyvinyl polymers). Examples of spreading agents and wetting agents include glycerin and polyethylene glycol, examples of stabilizers include phenol type antioxidants such as BHT (2,6-di-tert-butyl-4-methyphenol), BHA (mixture of 2-tert-butyl-4-methoxyphenol and 3-tert-butyl-4-methoxyphenol), amine type antioxidants such as diphenylamine, organic sulfur type antioxidants such as 2-mercaptobenzimidazole and the other antioxidants such as tocopherol and γ-oryzanol. Examples of preservatives include methyl paraoxybenzoate, ethyl parathionobenzoate, propyl parathionobenzoate and butyl paraoxybenzoate.

The cream formulation of Compound [A] for the present repelling method can be prepared by mixing Compound [A] with at least one carrier selected from non-volatile hydrocarbons (e.g. liquid paraffin, vaseline, squalane, microcrystalline wax), spermaceti, bees wax, hydrous lanolin, higher fatty acids, fatty acid esters, various animal oils and vegetable oils and silicone oils; and optionally water, polyhydric alcohols (e.g. glycols, glycerin, sorbitols), oil-soluble emulsifiers (e.g. sorbitan fatty acid, polyoxyethylene alkyl ethers, polyoxyethylene fatty acids, polyoxyethyleneglycol fatty acids), perfume, humectant, antioxidant, borax and UV-absorbent.

The emulsifiable concentrates and wettable powders obtained above are usually utilized after diluting with water to make the concentration of Compound [A] to 0.01–10% by weight. The oil solution and cream formulation are usually utilized as they are.

Further, Compound [A] or its liquid formulation can be used as a microencapsulated form.

In the present repelling method, it is possible to use the combination of Compound [A] with the other repellent including carane-3,4-diol, DEET, p-menthane-3,8-diol, 2,3,4,5-bis($\Delta^2$-butylene)tetrahydrofurufural, dipropyl isocinchomeronate, dibutyl succinate, MGK874 and N-(sec-butoxycarbonyl)-2-(2-hydroxyethyl)piperidine (KBR3023).

Compound [A] or its formulation, namely the present repellent, is applied to a place where it is desired to repel arthropods.

In order to repelling blood-sucking arthropods, the present repellent can be applied to humans or animals, usually on the skin. It may be directly applied to skin, or clothes on which Compound [A] is supported may be utilized for protecting humans or animals from blood-sucking of mosquitoes, flies, acarina and so on by covering exposed skin.

In order to repelling insanitary arthropods such as cockroaches and houseflies or unpleasant arthropods such as centipedes and pill bugs, the present repellent can be applied to buildings, offices, stores, houses and so on from getting indoors of the arthropods.

When the present repellent is applied to humans or animals, the amount of the treated Compound [A] is usually 0.1 to 50 g, preferably 1 to 10 g per 1 $m^2$ of the skin. When the present repellent is applied to a place where arthropods may invade, the amount of the treated Compound [A] is usually 10 mg to 10 g, preferably 100 mg to 1 g per 1$m^2$ of the treated area.

Preferable amount in which the present repellent can give effective results may be varied by type of formulation, kind and density of objective arthropods, used time, weather condition, age of applied man or animal, and so on. Therefore, the treated amount is suitably increased or decreased in the range described above.

A sheet, film, net, band or the like material treated the present repellent by spreading, soaking, kneading, dropping and so on, can be used by covering exposed skin, clothes or the place where arthropods may invade. Typical examples include nets, stockings, caps and hats for protecting skin of the humans by covering directly; nets for window screens in houses; interior curtains, reed screen and mosquito curtain; repellent sheets for covering floors or tables; and repellent tapes for pasting on adhesive side.

When arthropod-repellent molded resin is prepared by making the resin contain Compound [A], examples of the used materials include polyethylene; polypropylene; copolymers of ethylene and a monomer having polar group such as ethylene-vinyl acetate copolymer, ethylene-methyl (meta) acrylate copolymer, ethylene-ethyl acrylate copolymer, ethylene-vinyl acetate-methyl (meta)acrylate copolymer and so on; and synthetic resins containing chlorine such as polyvinyl chloride, polyvinylidene chloride and so on.

Among them, ethylene-vinyl acetate copolymer and ethylene-methyl metacrylate copolymer are preferable in view of absorption, spread and stability of the present compound and thermoforming (low-temperature processing) character.

To make a synthetic resin contain Compound [A], Compound [A] itself or a solution dissolving it with a suitable solvent such as acetone may be impregnated with a material of the synthetic resin, or Compound [A] and the synthetic resin may be melt and kneaded. In the latter case, Compound [A] is melt and kneaded with the synthetic resin at a high concentration in advance to prepare a master pellet. The master pellet or its dilution with a synthetic resin material having an objective content can be processed to a desirable form such as film, sheet, net and so on by usual process for thermoplastic resin such as injection mold, inflation technique and melt process such as spinning. Multiplayer molding and composite spinning may be available according to the objects such as controlling the effective period for preventing arthropods from invading.

EXAMPLES

The present invention will be further illustrated in more details by the production examples and test examples, although the present invention is not limited in any sense to these examples. Parts represent parts by weight.

Production Example 1

In 2 ml of ethanol, 66.7 mg of Compound [A] were dissolved to give an ethanol solution.

Production Example 2

In 5ml of acetone, 25 mg of Compound [A] were dissolved to give an acetone solution.

Production Example 3

Twenty parts of Compound [A] are dissolved in 65 parts of xylene. Fifteen parts of Sorpol 3005X (emulsifier, registered trademark of Toho Chemical) are added thereto, and stirred and mixed well to give a 20% emulsifiable concentrate.

Production Example 4

Forty parts of Compound [A] are mixed with 5 parts of Sorpol 5060 (registered trademark of Toho Chemical Co., Ltd.) and then with 32 parts of Carplex #80 (registered trademark of Shionogi & Co., Ltd.; fine powder of synthetic hydrated silicon oxide) and 23 parts of 300-mesh diatomaceous earth, and stirred with a juice mixer to give 40% wettable powders.

Production Example 5

A mixture of 10 parts of Compound [A], 10 parts of phenylxylylethane and 0.5 part of Sumidule L-75 (tolylenediisocyanate provided by Sumitomo Bayer Urethane Co., Ltd.) is added to 20 parts of a 10% aqueous solution of gum arabic, and stirred with a homomixer to give an emulsion having the mean particle diameter of 20 μm. The emulsion is further mixed with 2 parts of ethylene glycol and allowed to react on a water bath of 60° C. for 24 hours to give a microcapsule slurry.

A thickner solution is prepared by dispersing 0.2 part of xanthan gum and 1.0 part of Veegum R (aluminum magnesium silicate provided by Sanyo Chemical Co., Ltd.) in 56.3 parts of ion-exchanged water.

Forty-two and a half parts (42.5 parts) of the above microcapsule slurry and 57.5 parts of the above thickner solution are mixed to give a 10% microencapsulated formulation.

Production Example 6

A half (0.5) part of Compound [A] is dissolved in 10 parts of dichloromethane. The solution is mixed with 89.5 parts of Isopar M (isoparaffin produced by Exxon Chemical) to give a 0.5% oil solution.

Production Example 7

Ten parts of stearic acid, 2 parts of cetyl alcohol, 1 part of lanolin, 2 parts of liquid paraffin and 62 parts of water are added to 10 parts of Compound [A], melt and mixed under heating. Thirteen parts of heated glycerin are added thereto and mixed well to give a cream formulation.

Production Example 8

Twenty parts of ethanol, 15 parts of propylene glycol, 0.5 part of Tween 60 (polyoxyethylenesorbitan monostearate produced by ICI Company), and 0.5 part of triethanolamine are added to 6 parts of Compound [A], stirred and dissolved. Fifty-eight parts of water are added thereto to give an emulsifiable concentrate.

Production Example 9

Twelve and a half (12.5) parts of Compound [A] are dissolved in 87.5 parts of acetone. Eighty milliliters (80 ml) of the obtained solution are impregnated with 1 m² of filter paper and dried to give a repellent sheet.

Production Example 10

Thirty parts of Compound [A] and 70 parts of ethylene-methyl metacrylate copolymer (Acryft WH202 produced by Sumitomo Chemical) are mixed and kneaded with a closed press kneader for about 15 minutes, and make the mixture pellet to give a masterpellet. One hundred parts of the masterpellet and 200 parts of ethylene-methyl metacrylate copolymer are kneaded with a closed press kneader for more 15 minutes, supplied to extruder and made hot-cut while extruded to give a pellet containing 10% by weight of Compound [A]. The pellet is molded with T die extruder to give a repellent sheet having 1 mm of thickness.

Next, a method for preparing Compound [A] is shown as Reference preparation example.

Reference Preparation Example

Ten grams (10.0 g, 79.3 mmol) of 4-hydroxy-6-methyl-2-pyrone were suspended in 100 ml of toluene at room temperature. To the suspension, 1.22 g (10.0 mmol) of N,N-dimethylaminopyridine, 10.0 g (86.1 mmol) of isocaproic acid and 18.5 g (89.7 mmol) of dicyclohexylcarbodiimide were added subsequently. The mixed solution was stirred for 1 hour at room temperature, and then heated to 70° C. and stirred for 20 hours under heating. After the mixed solution was allowed to stand at room temperature, the precipitated insoluble dicyclohexylurea was filtered off, and washed with 1N hydrochloric acid once and 10% brine twice. The organic layer was dried over anhydrous magnesium sulfate and evaporated under reduced pressure to give a crude oily product.

The crude oily product was subjected to silica gel column chromatography (eluent: hexane/ethyl acetate=6/1) to give 7.11 g of Compound [A] (yield 40%).

$^1$H-NMR (CDCl$_3$/TMS): 0.94(6H, d), 1.54(2H, q), 1.63(1H, m), 2.27(3H, s), 3.08(2H, t), 5.93(1H, s), 17.88(1H, s)

Test Example 1

Fifty adult yellow fever mosquitoes (Aedes aegypti, approximately equal number of female and male) which were about 3 weeks old after emergence were released in a cage (22 cm×22 cm×30 cm, made of stainless steel and nylon gauze).

A chick whose abdominal feathers had been removed with haircutter was fixed on a wood board (7 cm×15 cm) having a hole of 2.5 cm×4 cm so that its abdominal skin was exposed. Next, the ethanol solution (90 μl) prepared according to Production example 1 was treated on the exposed area of the chick. The chick treated the solution on its abdomen was put on the cage, and the treated abdomen was exposed to the cage just after treating and after 3 hours from treating. After 1, 2 and 4 minutes from putting the chick, the number of yellow fever mosquitoes on the abdomen was counted and summed up. The test was repeated twice.

Further, the same procedure was performed using a chick treated ethanol without active ingredient on its abdomen, and the number of yellow fever mosquitoes on the abdomen was counted. From these results, repellency was calculated according to the following equation.

$$\text{Repellency (\%)} = \left(1 - \frac{\text{No. of attracted mosquitoes at repellent-treated chick}}{\text{No. of attracted mosquitoes at untreated chick}}\right) \times 100$$

Furthermore, the same procedure was performed using ethanol solution (90 μl) prepared according to Production example 1, provided that DEET was used in place of Compound [A] for comparison. The results were given in Table 1.

TABLE 1

| Active ingredient | Dosage (g/m²) | Immediately after treating | | After 3 hours | |
|---|---|---|---|---|---|
| | | No. of mosquitoes* | Repellency (%) | No. of mosquitoes* | Repellency (%) |
| Compound [A] | 3 | 0 | 100 | 0 | 100 |
| DEET | 3 | 0 | 100 | 3 | 96.5 |
| NO | — | 58 | — | 85 | — |

*Sum of yellow fever mosquitoes on the abdomen of the chick after 1, 2 and 4 minutes from treating.

Test Example 2

A triangular pillar (3 cm-equilateral triangle of opening, 6 cm in length) was prepared with filter paper, and the acetone solution (0.9 ml) prepared according to Production example 2 was impregnated with the triangular pillar uniformly and air-dried for 5 to 10 minutes.

In a 650 cc volume plastic cup, said triangular pillar was placed horizontally, German cockroaches (Blattella germanica, 5 males and 5 females) were placed in said plastic cup, covered with nylon gauze, and then observed the number of German cockroaches in the triangular pillar 24 hours later. The test was repeated twice.

Further, the same procedure was performed using a triangular pillar of filter paper impregnated acetone without active ingredient, and the number of German cockroaches in the triangular pillar 24 hours later was counted. From these results, repellency was calculated according to the following equation.

$$\text{Repellency (\%)} = \left(1 - \frac{\text{No. of cockroaches in repellent-treated triangular pillar}}{\text{No. of cockroaches in untreated triangular pillar}}\right) \times 100$$

Furthermore, the same procedure was performed using acetone solution prepared according to Production example 2, provided that DEET or MGK874 was used in place of Compound [A] for comparison. The results were given in Table 2.

TABLE 2

| Active ingredient | Dosage (mg/m$^2$) | No. of cockroaches* | Repellency (%) |
|---|---|---|---|
| Compound [A] | 833 | 2 | 90 |
| DEET | 833 | 20 | 0 |
| MGK874 | 833 | 17 | 15 |
| NO | — | 20 | — |

*: German cockroaches in the triangular pillar

What is claimed is:

1. A method for repelling arthropods which comprises applying an effective amount of 4-hydroxy-6-methyl-3-(4-methylpentanoyl)-2-pyrone to a place where it is desired to repel arthropods.

2. A method for repelling blood-sucking arthropods according to claim 1, wherein 4-hydroxy-6-methyl-3-(4-methylpentanoyl)-2-pyrone is applied to humans or animals.

3. A method for repelling blood-sucking arthropods according to claim 2, wherein the blood-sucking arthropods are mosquitos.

4. A method for repelling insanitary arthropods, wherein 4-hydroxy-6-methyl-3-(4-methylpentanoyl)-2-pyrone is applied to a place where the insanitary arthropods will invade.

5. A method for repelling insanitary arthropods according to claim 4, wherein the insanitary arthropods are cockroaches.

* * * * *